United States Patent
Kim

(10) Patent No.: US 9,649,011 B2
(45) Date of Patent: May 16, 2017

(54) APPARATUS FOR CLEANING AND STERILIZING INTERIOR OF SHOE

(71) Applicants: Young-Do Kim, Sejong-si (KR); DUREMAEUL CO., LTD., Sejong-si (KR)

(72) Inventor: Young-Do Kim, Sejong-si (KR)

(73) Assignees: YOUNG-DO Kim, Sejong-si (KR); DUREMAEUL CO., LTD., Sejong-si (KR)

(*) Notice: Subject to any disclaimer, the term of this patent is extended or adjusted under 35 U.S.C. 154(b) by 370 days.

(21) Appl. No.: 14/547,888

(22) Filed: Nov. 19, 2014

(65) Prior Publication Data

US 2015/0136184 A1    May 21, 2015

(30) Foreign Application Priority Data

Nov. 20, 2013  (KR) .......................... 10-2013-0141581

(51) Int. Cl.
| | |
|---|---|
| *B08B 3/02* | (2006.01) |
| *A61L 2/22* | (2006.01) |
| *A47L 23/02* | (2006.01) |
| *A47L 23/18* | (2006.01) |
| *A61L 2/08* | (2006.01) |
| *A61L 2/18* | (2006.01) |

(52) U.S. Cl.
CPC .............. *A47L 23/02* (2013.01); *A47L 23/18* (2013.01); *A61L 2/085* (2013.01); *A61L 2/18* (2013.01); *A61L 2/22* (2013.01); *B08B 3/02* (2013.01); *A61L 2202/15* (2013.01)

(58) Field of Classification Search
None
See application file for complete search history.

(56) References Cited

U.S. PATENT DOCUMENTS 2,201,548 A  *  5/1940  Treinis ..................... A61L 2/10
                                                                  250/455.11

FOREIGN PATENT DOCUMENTS

| KR | 20-0205500 Y1 | 12/2000 | |
| KR | 2020010037375 | * 3/2002 | ............. A47L 23/00 |

OTHER PUBLICATIONS

Machine Translation for Korean App. No. 2002683680000.*

* cited by examiner

*Primary Examiner* — Michael Barr
*Assistant Examiner* — Rita Adhlakha
(74) *Attorney, Agent, or Firm* — Novick, Kim & Lee, PLLC; Jae Youn Kim

(57) ABSTRACT

An apparatus for cleaning and sterilizing an interior of a shoe which generates ultrasonic wind of a whirlwind type in the interior of the shoe to remove foreign substances from the interior of the shoe and which injects ultra fine particles of solution into the interior of the shoe to sterilize the interior of the shoe. The apparatus includes a housing opened or closed with a door; a shoe supporting member mounted on a top end of a support pillar having a predetermined length and vertically installed in an inner space of the housing, wherein the show supporting member is configured to be inside the shoe and support the shoe by hanging the shoe thereto; a vibration guide pipe fixed to an inside of the shoe supporting member; and a nozzle tube movably installed in the vibration guide pipe.

8 Claims, 6 Drawing Sheets

APPARATUS FOR CLEANING AND STERILIZING INTERIOR OF SHOE

BACKGROUND OF THE INVENTION

1. Field of the Invention

The present invention relates to an apparatus for cleaning and sterilizing an interior of a shoe, and more particularly, to an apparatus for cleaning and sterilizing an interior of a shoe which generates ultrasonic wind of a whirlwind type in the interior of the shoe to remove foreign substances from the interior of the shoe and which injects ultra fine particles of germicide solution into the interior of the shoe at a high pressure to sterilize the interior of the shoe, so that the interior of shoe may be hygienically and cleanly maintained.

2. Description of the Related Art

In general, foreign substances may be introduced into shoes through the inlets of the shoes and the shoes may be contaminated with socks. In addition, when walking or doing exercise, the interiors of the shoes may be easily contaminated by perspiration of foots, the shoes may be poor in sanitary conditions. Since the interior of a shoe is deeply formed from the inlet, it is difficult to clean or sterilize the interior of a shoe due to the structural property.

There is disclosed a related art of the present invention in Korean Utility Model Registration No. 20-020500 entitled "Apparatus for washing interior of shoe". The apparatus disclosed in the related art includes a receiving unit including an injection pump for supplying detergent liquid for cleaning an interior of a shoe, and a motor for driving an absorbing pump for absorbing sewage and waste water generated after cleaning the shoe; a main body including a detergent liquid tank for reserving the detergent liquid and a partition wall for forming an isolation space between the detergent liquid and a sewage and waste water tank for reserving the collected sewage and waste water; an exhaust pipe provided with an exhaust valve plate installed to the injection pump fixed in a receiving part of the main body, wherein the exhaust valve plate is opened by a pressure of the detergent liquid supplied by the injection pump and is closed by a pressure of the absorbed sewage and waste water; an absorbing pipe provided with an absorbing valve installed to the absorbing pump, wherein the absorbing valve is opened by a pressure of the absorbed sewage and waste water; and a handle provided with a switch for driving a motor, wherein the exhaust pipe is connected to the absorbing pipe; and a brush provided with a plurality of through-holes for supplying the detergent liquid and collecting the sewage and waste water and connected to one side of the handle through a connecting pipe.

As described above, according to the apparatus for cleaning an interior of a shoe, the interior of the shoe is cleaned by injecting water so that a lot of water is spent. In addition, since it is necessary to dry the cleaned shoe, much time is elapsed. Specifically, it is impossible to clean leather shoes a problem. Thus, there is a need to provide an apparatus for cleaning an interior of a shoe which can simply clean shoes to immediately wear the cleaned shoes and in addition, clean even leather shoes without any problems to cleanly and hygienically wear the leather shoes.

SUMMARY OF THE INVENTION

The present invention has been made to solve the above problems occurring in the related art, and an object of the present invention is to provide an apparatus for cleaning and sterilizing an interior of a shoe, which includes a shoe supporting member installed in an inner space of a housing which may opened or closed with a door in order to support the shoe by hanging the shoe thereon, a nozzle tube movably installed on a central axis of a vibration guide pipe having a gradually enlarged inlet in a horizontal direction and formed of a hose having a predetermined length, and an elastic buffering ring coupled to the nozzle tube. Thus, compressed air and sterilizing chemical solution are mixed at a rear end of the nozzle tube and the mixture is sprayed through the nozzle tube, so a vibration operation occurs as the nozzle tube collides with an inner wall surface of the vibration guide pipe at a high speed, so that ultrasonic air and fine particles of germicide solution are sprayed into the interior of the shoe, thereby cleaning and sterilizing the interior of the shoe.

According to the present invention, there is provided an apparatus for cleaning and sterilizing an interior of a shoe, which includes a housing opened or closed with a door; a shoe supporting member mounted on a top end of a support pillar having a predetermined length and vertically installed in an inner space of the housing to support the shoe by hanging the shoe thereto; a vibration guide pipe fixed to an inside of the shoe supporting member; and a nozzle tube having a predetermined length, which is movably installed on a central axis of the vibration guide pipe in a horizontal state and formed of a hose, wherein compressed air and chemical solution are mixed at a rear end of the nozzle tube and sprayed through a front end nozzle of the nozzle tube so that the nozzle tube is subject to a vibration operation, causing the nozzle tube to innumerably collide with an inner wall surface of the vibration guide pipe.

The shoe supporting member has a radial shape with an opened front, and includes a vertical supporting piece having a through-hole to stably support the shoe and an angle adjusting unit to arbitrarily adjust an angle of the shoe supporting member.

The support pillar for fixing the shoe supporting member is vertically formed at a predetermined height.

A pair of support pillars is provided in opposition to each other and the shoe supporting member is installed to each of the support pillars.

The apparatus further includes an elastic buffering ring coupled to an outer periphery surface of the nozzle tube.

The vibration guide pipe has a bugle shape and an inlet of the vibration guide pipe is gradually enlarged.

The apparatus further includes a foreign substance collecting unit including a suction fan provided at one side of a low surface of the inner space of the housing.

The apparatus further includes an infrared sterilization lamp (80) installed at one side of an upper portion of the inner space of the housing.

According to the present invention, the ultrasonic wind of a whirlwind type and fine particles of germicide solution are inject into the interior of the shoe at a high pressure to remove foreign substances from the interior of the shoe and to sterilize the interior of the shoe, so that the functions of separating and decomposing the foreign substances from the interior of the shoe may be effectively performed. In addition, the fine particles of germicide is uniformly introduced to perform the sterilizing function at the maximum while rarely leaving moisture in the shoe, even the interior of a leather shoe may be rapidly cleaned and sterilized, a user can instantly wear the shoe, and the interior of the shoe may be cleanly and hygienically maintained.

DETAILED DESCRIPTION OF THE INVENTION

Figure 1:
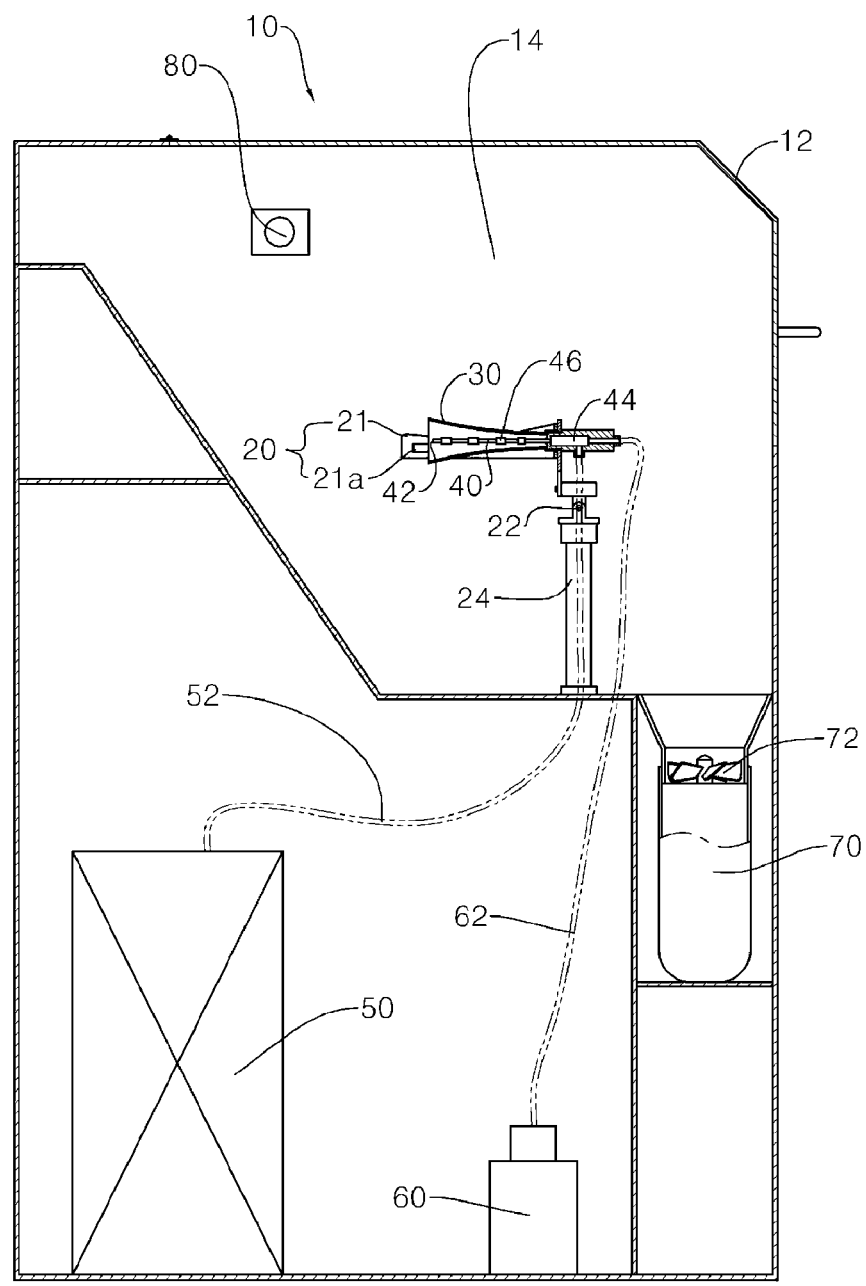
FIG. 1 is a sectional view showing an apparatus for cleaning and sterilizing an interior of a shoe according to an embodiment of the present invention.
Figure 2:
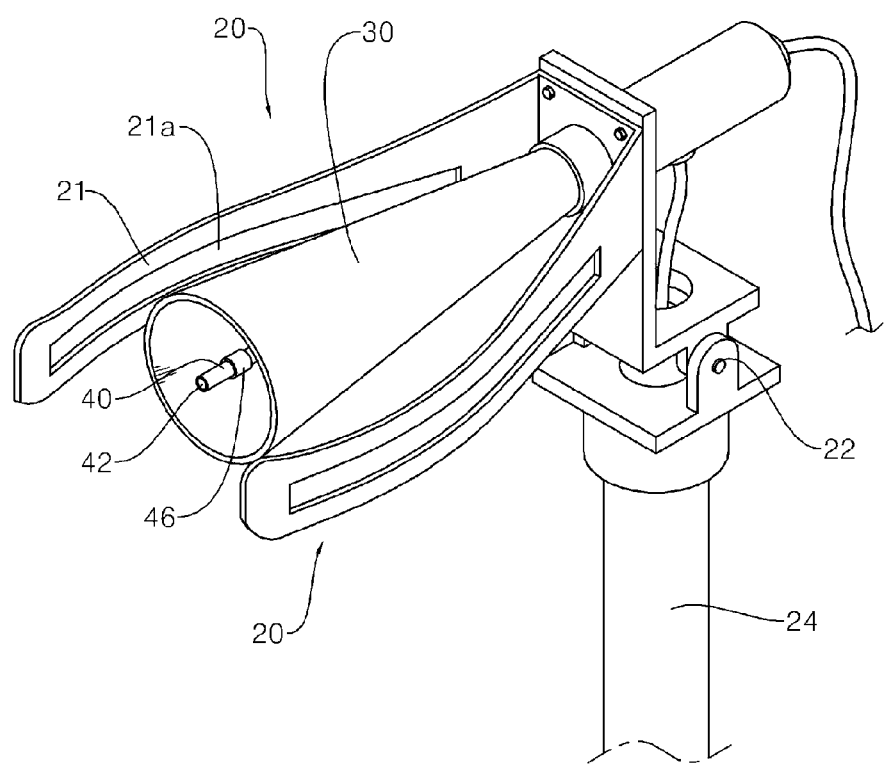
FIG. 2 is a perspective view showing a shoe supporting member of an apparatus for cleaning and sterilizing an interior of a shoe according to an embodiment of the present invention.
Figure 3:
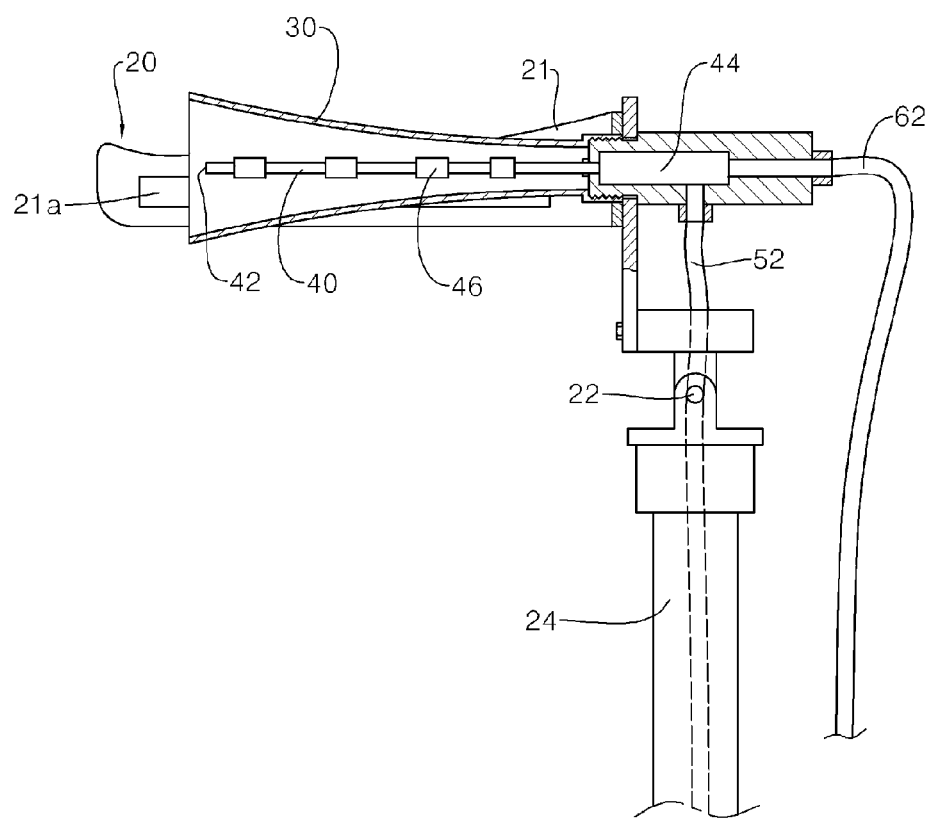
FIG. 3 is an enlarged sectional view showing a nozzle tube of an apparatus for cleaning and sterilizing an interior of a shoe according to an embodiment of the present invention.
Figure 4:
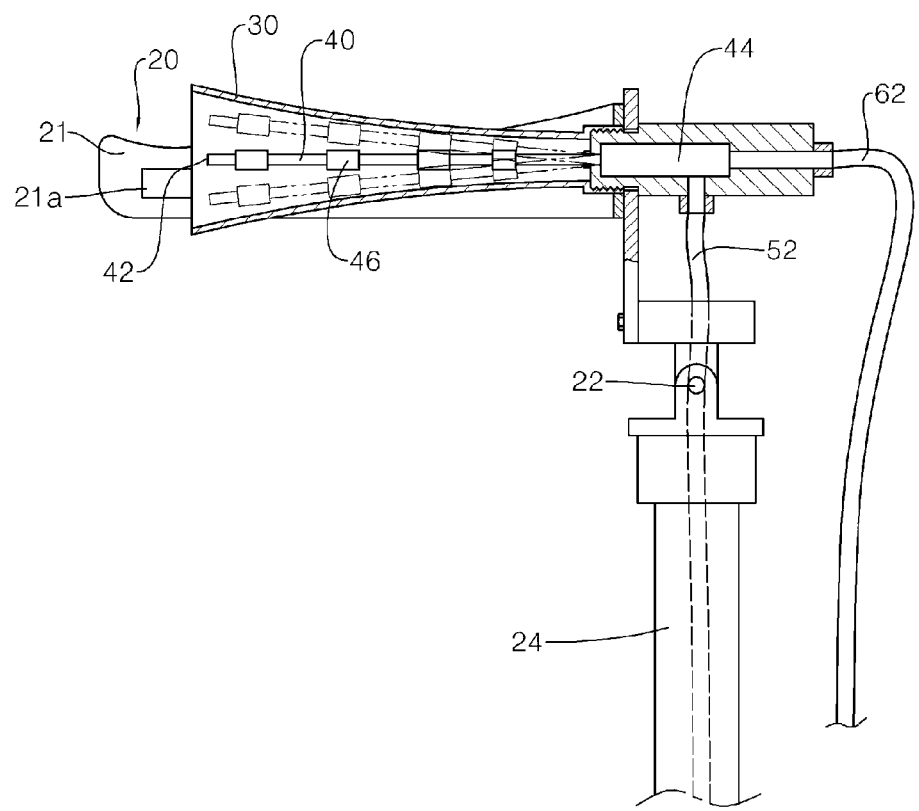
FIG. 4 is a sectional view illustrating a vibration operation of a nozzle tube in an apparatus for cleaning and sterilizing an interior of a shoe according to an embodiment of the present invention.
Figure 5:
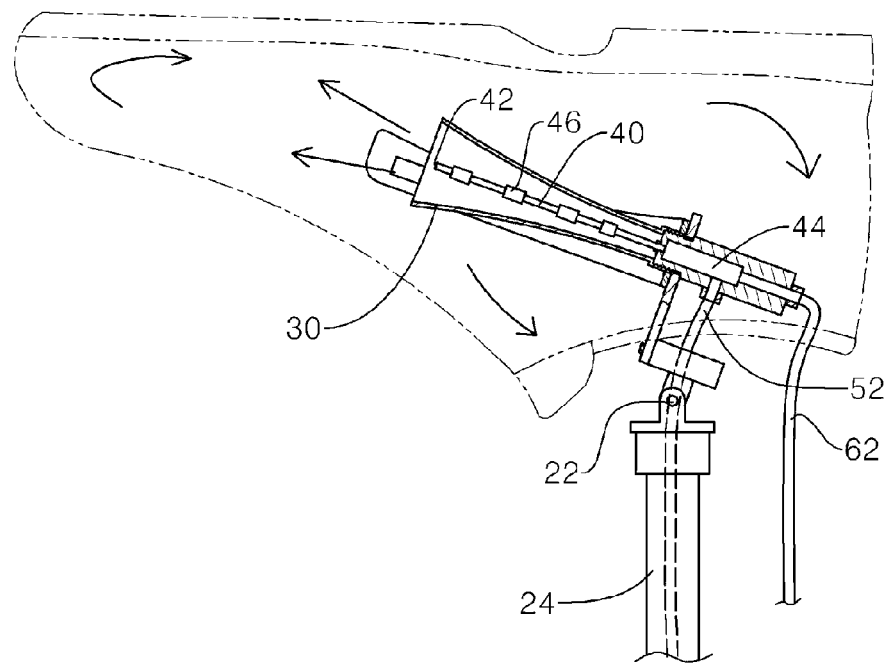
FIG. 5 is a longitudinal sectional view illustrating a state of using an apparatus for cleaning and sterilizing an interior of a shoe according to an embodiment of the present invention.
Figure 6:
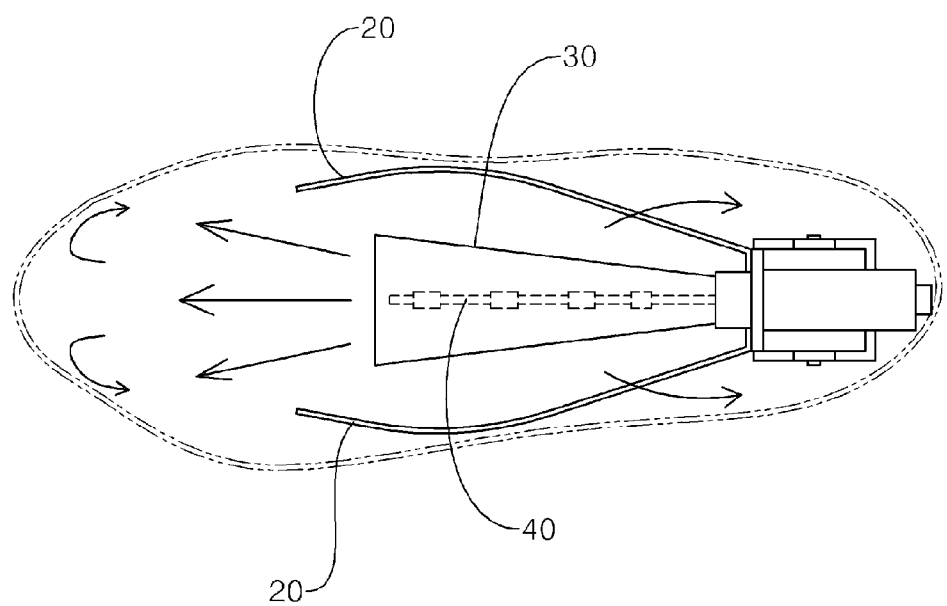
FIG. 6 is a cross-sectional view illustrating a state of using an apparatus for cleaning and sterilizing an interior of a shoe according to an embodiment of the present invention.
Figure 7:
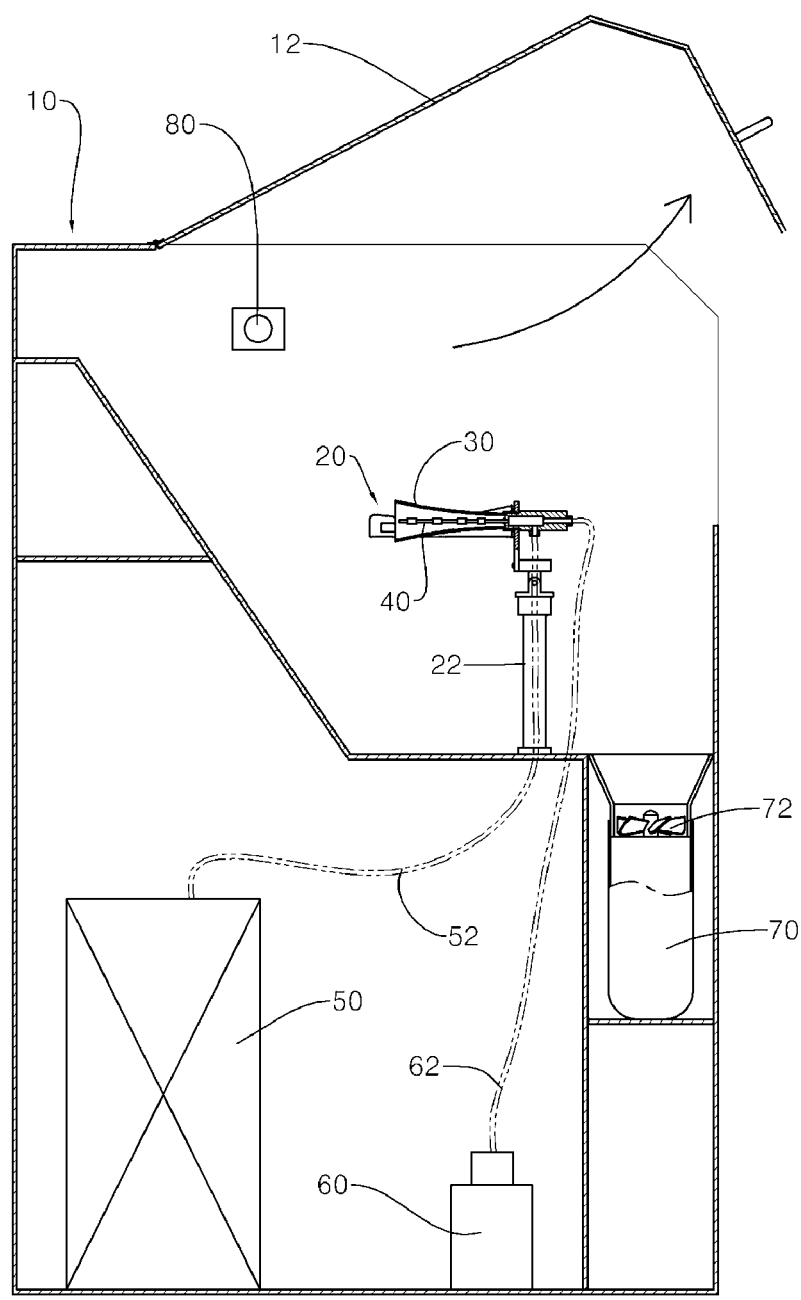
FIG. 7 is an exemplary sectional view showing the opened door of an apparatus for cleaning and sterilizing an interior of a shoe according to an embodiment of the present invention.

Hereinafter, preferable embodiments of the present invention will be described in detail with reference to accompanying drawings. In the following description, if detailed description about well-known functions or configurations may make the subject matter of the disclosure unclear, the detailed description will be omitted.

An apparatus for cleaning and sterilizing an interior of a shoe according to the present invention includes a housing 10 opened or closed with a door 12, a shoe supporting member 20 mounted on a top end of a support pillar 24 in an inner space 14 of the housing 10 in order to support the shoe by hanging the shoe on the shoe supporting member 20, wherein the support pillar 24 stands up with a predetermined length, a vibration guide pipe 30 fixed to an inside of the shoe supporting member 20 and having a gradually enlarged inlet; and a nozzle tube 40 movably installed on a central axis of the vibration guide pipe 30 in a horizontal direction and formed of a hose having a predetermined length, the nozzle tube 40 having a predetermined length, wherein compressed air and germicide solution are mixed at a rear end of the nozzle tube 40 and sprayed through a front end nozzle 42 of the nozzle tube 40 to generate a vibration operation such that the nozzle tube 40 collides with an inner wall surface of the vibration guide pipe 30. Thus, ultrasonic air is injected to spray fine particles of germicide solution into the interior of the shoe, so that foreign substances are removed from the interior of the shoe and the interior of the shoe is sterilized.

The inner space 14 of the housing 10 is shut off from an outside. The shoe may be drawn into or out from the inner space through the door 12. The foreign substances, which are generated while the shoe is cleaned in the interior space 14 shut off from an outside, are prevented from being scattered to an outside.

The shoe supporting member 20 has an opened front with a radial shape. The shoe supporting member 20 includes a vertical supporting piece (21) which may stably support the shoe and is provided with a through-hole (21a) through which wind may be uniformly transferred therein. In addition, the shoe supporting member 20 includes an angle adjusting unit 22 for arbitrarily adjusting an installation angle of the shoe supporting member 20, such that the shoe may be easily installed thereto or separated therefrom without regard to any kinds of shoes.

A support pillar 24 for fixing the shoe supporting member 20 has a predetermined length to allow a shoe having a long neck, such as a boot, to be installed to the shoe supporting member 20 and is vertically formed at a height corresponding to the predetermined length. At least one pair of support pillars 24 may be provided at places to face each other and the shoe supporting members 20 are installed to the support pillars 24, respectively, so that both shoes may be cleaned and sterilized together.

The vibration guide pipe 30 has a bugle shape, such that an inlet of the vibration guide pipe 30 is gradually enlarged. When the nozzle tube 40 vibrates to collide with an inner wall surface of the vibration guide pipe 30 at a high speed, a front end nozzle 42 of the nozzle tube 40 spins at a long radius as a whirlwind, so that wind may uniformly make contact with the entire interior of the shoe.

The nozzle tube (40) is a thin hose having a predetermined length, so that the nozzle tube 40 is horizontally maintained in a normal state. When compressed air is sprayed at a high pressure through the nozzle tube 40, high mobility is applied to the nozzle tube 40 while the compressed air is passing through the nozzle tube 40, so that the nozzle body 40 may collide with the inner wall of the vibration guide pipe 30 at a high speed, thereby causing vibration operation. An elastic buffering ring 46 is coupled to an outer periphery surface of the nozzle tube 40. When the nozzle tube 40 collides with the vibration guide pipe 30, the elastic buffering ring 46 performs a buffering function and facilitates the vibration operation.

In addition, a confluent tube 44, to which a compressed air supply pipe 52 and a chemical solution supply pipe 62 are connected, is provided at a rear end of the nozzle tube 40. The chemical solution supplied from a chemical solution supply tank 60 is absorbed in the confluent tube 44 by a popping pressure of the compressed air supplied from a compressed air supply unit 50, so that the chemical solution is mixed with air in the nozzle tube 40 and sprayed through the nozzle tube 40. A very little amount of chemical solution may be supplied to the chemical solution supply pipe 62.

The compressed air supply unit 50 may be a typical compressor and uses compressed air such as nitride gas. Since, the chemical solution supply tank 60 can use not only the chemical solution for sterilizing the interior of the shoe, but also the chemical solution having the deodorization function, the present invention may include various types of chemical solutions which may be sprayed into the interior of the shoe. Thus, the present invention may have the sterilizing and deodorizing functions.

In addition, a foreign substance collecting unit 70 including a suction fan 72 is provided at one side of a low surface of the inner space 14 of the housing 10, such that the foreign substances generated while washing the interior of the shoe may be collected and easily separated and processed, so the outer skin of the shoe or the inner space 14 may be prevented from being polluted due to the scattering of the foreign substances.

Preferably, an infrared sterilization lamp 80 may be installed at one side of an upper portion of the inner space 14 of the housing 10 to sterilize the outer skin of the shoe and to prevent the inner space 14 where the shoe cleaning is performed from being polluted.

As described above, according to the present invention, after a shoe is installed to the shoe supporting member 20 while the bottom surface of the shoe faces upward so that the shoe is stably supported by the shoe supporting member 20, if the compressed air and the germicide solution are supplied through the compressed air supply pipe 52 and the chemical solution supply pipe 62 connected to the rear end of the nozzle tube 40, the compressed air and the germicide solution are mixed at the rear end of the nozzle tube 40 and spray through the nozzle 42 of the front end of the nozzle tube 40.

In this case, the nozzle tube 40 has mobility as the compressed air passes through the nozzle tube 40, so that the nozzle tube 40 is subject to the vibration operation, in which the nozzle tube 40 innumerably collides with the inner wall of the vibration guide pipe 30 at a high speed, so an ultrasonic wave is generated and the germicide solution mixed with the compressed air is converted into fine particles. Thus, foreign substances are finely decomposed and separated from the shoe due to the ultrasonic air sprayed into the interior of the shoe, thereby allowing the foreign substances to escape through the neck of the shoe. In addition, the germicide solution is uniformly permeated into the shoe by spraying the fine particles of germicide solution, so that the sterilization function may be maximized.

Since the nozzle tube 40 vibrates to collide with an inner wall surface of the vibration guide pipe 30, which has the bugle shape and the inlet gradually enlarged, at a high speed, the ultrasonic air and the fine particles of germicide spin as a whirlwind, so that it may be encouraged that the germicide uniformly makes contact with the entire interior of the shoe.

In addition, since a very little amount of germicide solution is supplied from the chemical solution supply tank 60 and is converted into fine particles, even if the germicide makes contact with the interior of the shoe and is permeated into the shoe to sterilize the shoe, moisture may rarely remain in the shoe, so a user can instantly wear the shoe without any additional drying operations after cleaning the shoe.

Meanwhile, the foreign substances exhausted to an outside of the shoe through the neck of the shoe during the process of cleaning the shoe are collected into the foreign substance collecting unit 70 by the suction fan 72 provided on the bottom surface of the space 14.

Although an exemplary embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. An apparatus for cleaning and sterilizing an interior of a shoe, the apparatus comprising:
    a housing opened or closed with a door;
    a shoe supporting member mounted on a top end of a support pillar having a predetermined length and vertically installed in an inner space of the housing, wherein the shoe supporting member is configured to be inside the shoe and to support the shoe by hanging the shoe thereto;
    a vibration guide pipe fixed to an inside of the shoe supporting member; and
    a nozzle tube having a predetermined length, which is movably installed on a central axis of the vibration guide pipe in a horizontal state and formed of a hose, wherein compressed air and chemical solution are mixed at a rear end of the nozzle tube and sprayed through a front end nozzle of the nozzle tube so that the nozzle tube vibrates and collides with an inner wall surface of the vibration guide pipe.

2. The apparatus of claim 1, wherein the shoe supporting member has a radial shape with an opened front, and includes a vertical supporting piece having a through-hole to stably support the shoe and an angle adjusting unit to arbitrarily adjust an angle of the shoe supporting member.

3. The apparatus of claim 1, wherein the support pillar for fixing the shoe supporting member is vertically formed at a predetermined height.

4. The apparatus of claim 1, wherein the support pillar comprises a pair of support pillars in opposition to each other and the shoe supporting member is installed to each of the support pillars.

5. The apparatus of claim 1, further comprising an elastic buffering ring coupled to an outer periphery surface of the nozzle tube.

6. The apparatus of claim 1, wherein the vibration guide pipe has a bugle shape and an inlet of the vibration guide pipe is gradually enlarged.

7. The apparatus of claim 1, further comprising a foreign substance collecting unit including a suction fan provided at one side of a low surface of the inner space of the housing.

8. The apparatus of claim 1, further comprising an infrared sterilization lamp installed at one side of an upper 25 portion of the inner space of the housing.

* * * * *